(12) United States Patent
Setimi

(10) Patent No.: US 8,032,545 B2
(45) Date of Patent: Oct. 4, 2011

(54) SYSTEMS AND METHODS FOR REFINING IDENTIFICATION OF CLINICAL STUDY CANDIDATES

(75) Inventor: Philip D. Setimi, Chicago, IL (US)

(73) Assignee: General Electric Company, Schenectady, NY (US)

( * ) Notice: Subject to any disclaimer, the term of this patent is extended or adjusted under 35 U.S.C. 154(b) by 1151 days.

(21) Appl. No.: 11/561,240

(22) Filed: Nov. 17, 2006

(65) Prior Publication Data

US 2007/0294110 A1 Dec. 20, 2007

Related U.S. Application Data

(60) Provisional application No. 60/804,738, filed on Jun. 14, 2006.

(51) Int. Cl.
*G06F 7/00* (2006.01)
(52) U.S. Cl. ........................................................ 707/769
(58) Field of Classification Search .................. 707/705, 707/713
See application file for complete search history.

(56) References Cited

U.S. PATENT DOCUMENTS

| | | | | |
|---|---|---|---|---|
| 6,714,929 B1* | 3/2004 | Micaelian et al. | | 1/1 |
| 7,769,763 B1* | 8/2010 | Bem et al. | | 707/749 |
| 2002/0087408 A1* | 7/2002 | Burnett | | 705/14 |
| 2002/0169765 A1* | 11/2002 | Saltz | | 707/3 |
| 2005/0236474 A1* | 10/2005 | Onuma et al. | | 235/382 |
| 2006/0155688 A1* | 7/2006 | Chou | | 707/3 |
| 2006/0206471 A1* | 9/2006 | Tsuzuki et al. | | 707/3 |
| 2007/0136345 A1* | 6/2007 | Blazejewski et al. | | 707/101 |
| 2008/0162459 A1* | 7/2008 | Portnoy | | 707/5 |

OTHER PUBLICATIONS

UK Intellectual Property Office, Office Action for Application No. GB0711364.0, (4 pages) dated Oct. 18, 2010.

* cited by examiner

*Primary Examiner* — Angela Lie
(74) *Attorney, Agent, or Firm* — McAndrews, Held & Malloy, Ltd.; Armando Pastrana, Jr.

(57) ABSTRACT

Certain embodiments of the present invention provide systems and methods for refining the identification of study candidates. In an embodiment, the method may include receiving a plurality of clinical conditions at a user interface. The conditions may generally be tied to codified terms in electronic medical patient records. The method may also include receiving parameters for tailoring a search of electronic medical data for the clinical conditions. For example, the parameters may weight the conditions and may include ranking the conditions, determining whether the conditions are mandatory for the pool, and determining a percentage deviation for numerical ranges. The method may also include executing an optimization function to create a pool according to the specified conditions and parameters. The method may also include displaying the pool in an order from the most optimal results to the least optimal results.

20 Claims, 10 Drawing Sheets

910

| Condition | Rank | Percentage Deviation | Mandatory? |
|---|---|---|---|
| DIABETES | 1 | | YES |
| FAMILY HISTORY OF CORONARY ARTERY DISEASE | 2 | | YES |
| AGE = 25 - 30 | 3 | 10% | NO |
| GEOGRAPHY = IL | 4 | | NO |

920  930  940

915
Study Type
Study A

FIG. 8

| Condition |
|---|
| DIABETES |
| FAMILY HISTORY OF CORONARY ARTERY DISEASE |
| AGE = 25 - 30 |
| GEOGRAPHY = IL |

| Condition | Rank | Percentage Deviation | Mandatory? |
|---|---|---|---|
| DIABETES | 1 | | YES |
| FAMILY HISTORY OF CORONARY ARTERY DISEASE | 2 | | YES |
| AGE = 25 - 30 | 3 | 10% | NO |
| GEOGRAPHY = IL | 4 | | NO |

920  930  940

Study Type — 915

Study A

FIG. 10

| PATIENT 1010 | DIABETES 1020 | FAMILY HISTORY OF CORONARY ARTERY DISEASE 1030 | AGE = 25 - 30 1040 | GEOGRAPHY = IL 1050 |
|---|---|---|---|---|
| A | X | X | 26 | IL |
| B | X | X | 28 | IL |
| C | X | X | 30 | IL |
| D | X | X | 31 | IL |
| E | X | X | 19 | IL |
| F | X | X | 27 | TX |
| G | X | X | 19 | IL |
| H | X | X | 35 | CA |
| I | X | X | 18 | ME |

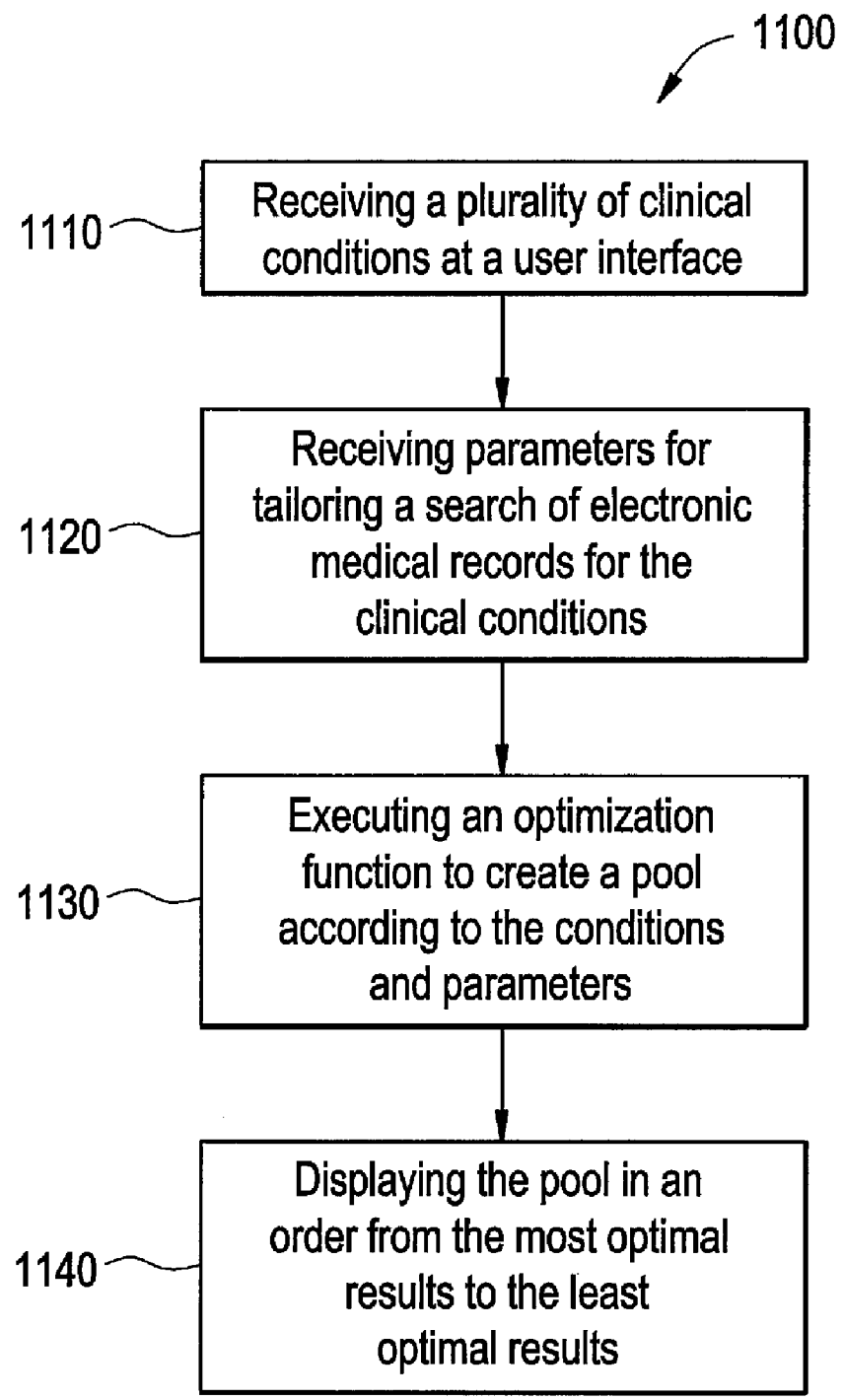

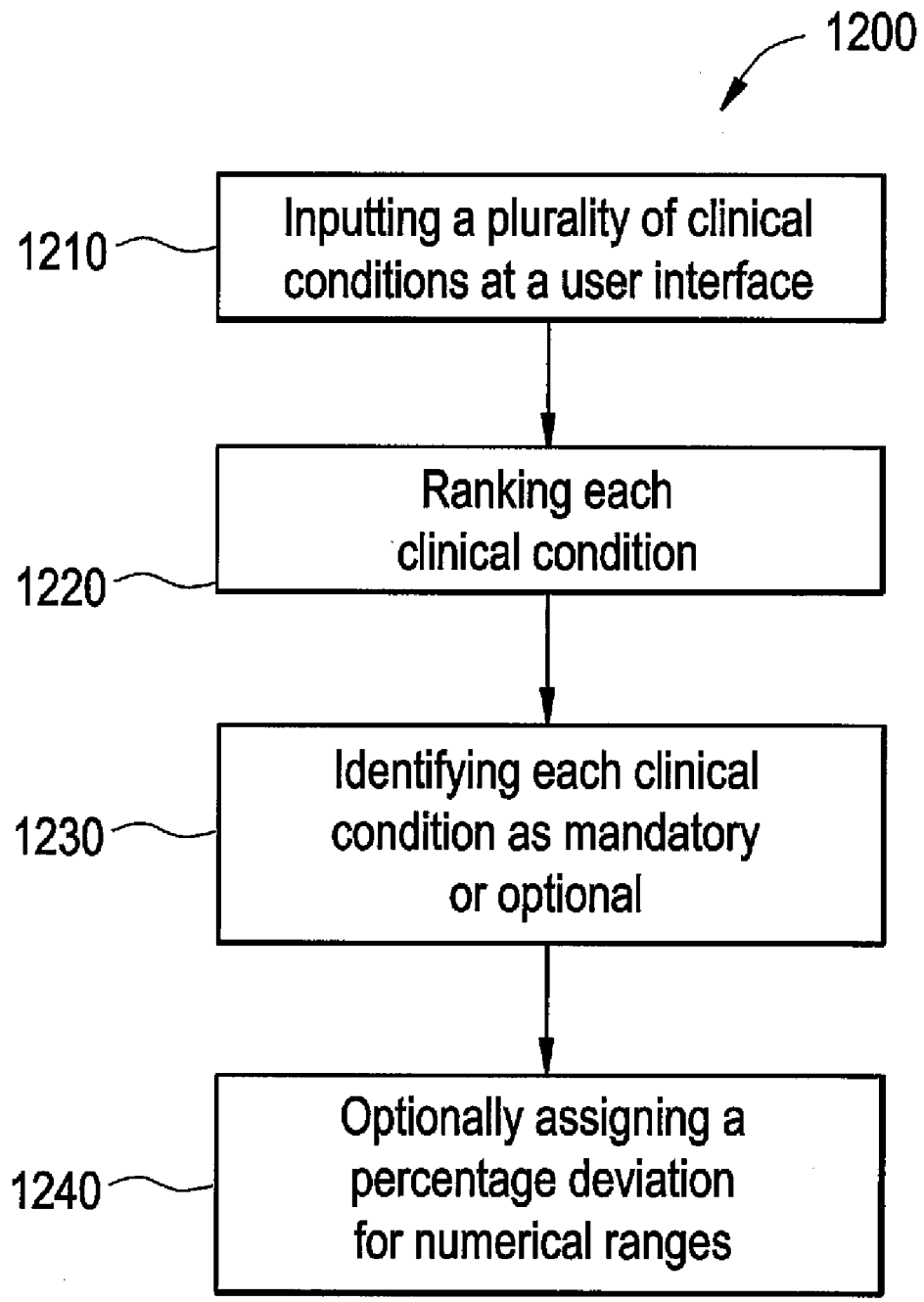

SYSTEMS AND METHODS FOR REFINING IDENTIFICATION OF CLINICAL STUDY CANDIDATES

RELATED APPLICATIONS

The application relates to and claims priority from U.S. Provisional Application No. 60/804,738, entitled "Systems and Methods for Refining Identification of Clinical Study Candidates," filed on Jun. 14, 2006, which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to search and analysis of electronic medical record data. More particularly, the present invention relates to refining the identification of clinical study candidates based on electronic medical record data.

Many aspects of the healthcare industry are becoming increasingly electronic in nature. Hospitals typically utilize computer systems to manage the various departments within a hospital and data about each patient is collected by a variety of computer systems. For example, a patient may be admitted to the hospital for a Transthoracic Echo (TTE). Information about the patient (e.g., demographics and insurance) could be obtained by the hospital information system (HIS) and stored on a patient record. This information could then be passed to the cardiology department system (commonly known as the cardio vascular information system, or CVIS), for example. Typically the CVIS is a product of one company, while the HIS is the product of another company. As a result, the database between the two may be different. Further, information systems may capture/retain and send different levels of granularity in the data. Once the patient information has been received by the CVIS, the patient may be scheduled for a TTE in the echo lab. Next, the TTE is performed by the sonographer. Images and measurements are taken and sent to the CVIS server. The reading physician (e.g., an echocardiographer) sits down at a review station and pulls the patient's TTE study. The echocardiographer then begins to review the images and measurements and creates a complete medical report on the study. When the echocardiographer completes the medical report, the report is sent to the CVIS server where it is stored and associated with the patient through patient identification data. This completed medical report is an example of the kind of report that could be sent to a data repository for public data mining. Medication instructions, such as documentation and/or prescription, as well as laboratory results and/or vital signs, may also be generated electronically and saved in a data repository.

Today, medical device manufacturers and drug companies face an ever-growing challenge in collecting clinical data on the real-life utilization of their products. As patient medical reports are becoming computerized, the ability to obtain real-life utilization data becomes easier. Further, the data is easier to combine and analyze (e.g., mine) for greater amounts of useful information.

As medical technology becomes more sophisticated, clinical analysis may also become more sophisticated. Increasing amounts of data are generated and archived electronically. With the advent of clinical information systems, a patient's history may be available at a touch of a button. While accessibility of information is advantageous, time is a scarce commodity in a clinical setting. To realize a full benefit of medical technological growth, it would be highly desirable for clinical information to be organized and standardized.

Even if clinical or image-related information is organized, current systems often organize data in a format determined by developers that is unusable by one or more medical practitioners in the field. Additionally, information may be stored in a format that does not lend itself to data retrieval and usage in other contexts. Thus, a need exists to structure data and instructions in a way that is easier to comprehend and utilize.

Data warehousing methods have been used to aggregate, clean, stage, report and analyze patient information derived from medical claims billing and electronic medical records (EMR). Patient data may be extracted from multiple EMR databases located at patient care provider (PCP) sites in geographically dispersed locations, then transported and stored in a centrally located data warehouse. The central data warehouse may be a source of information for population-based profile reports of physician productivity, preventative care, disease-management statistics and research on clinical outcomes. Patient data is sensitive and confidential, and therefore, specific identifying information must be removed prior to transporting it from a PCP site to a central data warehouse. This removal of identifying information must be performed per the federal Health Insurance Portability and Accountability Act (HIPAA) regulations. Any data that is contained in a public database must not reveal the identity of the individual patients whose medical information is contained in the database. Because of this requirement, any information contained on a medical report or record that could aid in tracing back to a particular individual must be removed from the report or record prior to adding the data to a data warehouse for public data mining.

Patient data may be useful to medical advancement, as well as diagnosis and treatment of patients, in a variety of ways. In order to accurately assess the impact of a particular drug or treatment on a patient, for example, it is helpful to analyze all medical reports relating to the particular patient. Removing data that can be used to trace back to an individual patient can make it impossible to group and analyze all medical reports relating to a particular patient. In addition, one of the aims of population analysis is to assemble an at-risk cohort population comprised of individuals who may be candidates for clinical intervention. De-identified data is not very useful to the patient care providers who need to know the identity of their own patients in order to treat them. Users of the system may need the ability to re-identify patients for further follow-up. Portal users may need to re-identify the patients in a process that doesn't involve the portal system, i.e. the process of re-identification occurs on the local user's system.

One avenue for medical advancement occurs through administration of clinical studies. Current identification of clinical study participants typically involves the use of mass media to broadcast a need for patients who fit a list of clinical conditions that would potentially qualify the candidate for clinical study. This manual, mass media-based selection process is lengthy and expensive due to the cost of using mass media and the time involving in crafting a message, broadcasting the message, and waiting for responses. Thus, systems and methods for identifying potential clinical study participants more rapidly would be highly desirable. Systems and methods for identifying potential clinical study participants with greater precision and less expense would also be highly desirable.

Currently, researchers design clinical study protocols using recent statistics on disease incidence and published literature on similar studies to best define clinical conditions or parameters that will yield a potential study pool of significant size and quality. Such protocol design is a 'trial and error' methodology. Use of trial and error protocol design methodologies involve great expense when a certain protocol has begun recruitment and requires alteration due to insignificant potential study participant volume, for example. Often, changes to the protocol require that all previously qualified patients must be re-screened based on the latest study parameters. Thus, systems and methods for improved adjustment of clinical study protocols and screening of potential clinical study participants would be highly desirable.

Using current methods, clinical study investigators are recruited for participation during the early phase of a study using a variety of methods, including mass media, databases, and word of mouth. The goal of the recruitment effort is to identify researchers with a clinical and research background who meet the study criteria and who also service a patient population large and focused enough to contain patients whose clinical backgrounds meet the study criteria. Often, a clinical study sponsor will phone clinical study investigators to gauge both interest and an estimate for the number of patients who meet study criteria. Frequently, this method of self-reporting over estimates the number of potential study candidates because these estimates are attained from the investigator's memory versus an actual patient medical record. By over-estimating the patient pool, the study may not meet its end-targets, may not reach statistical significance, may incur major expenses to urgently find more participants, may incur significant delays, and/or may require a total change of the study protocol and thus re-recruitment of participants.

Therefore, there is a need for systems and methods for improved clinical study definition and participant selection. There is a need for systems and methods for improved clinical trial configuration in compliance with HIPAA.

BRIEF SUMMARY OF THE INVENTION

Certain embodiments of the present invention may include a method for searching codified electronic medical data. The method may include receiving a plurality of conditions at a user interface. The method may also include receiving a plurality of parameters for tailoring a search of the codified electronic medical data. The parameters may be used to assign a weight to the conditions. The method may include searching the codified electronic medical data to create a pool of candidates according to the weighted conditions. The method may also include displaying the pool of candidates in order from the most optimal results to the least optimal results. The conditions may correspond with codified terms of the codified electronic medical data. The parameters may include ranking the conditions, a determination of whether particular conditions are mandatory, and a determination of a deviation for numerical ranges. The conditions and parameters may be based on a predetermined study type. The parameters may include determining a deviation for geographical ranges. A user may select a sub-set of the pool of candidates to retrieve contact information or medical records.

Certain embodiments of the present invention may include a system for identifying a pool of potential study participants. The system may include a user interface for allowing input of conditions and parameters. The parameters may be used to assign a weight to the conditions. The user interface may also facilitate inviting one or more of the pool of potential study participants to participate in a clinical study. The user interface may also include an input for a predetermined study type. The system may also include data storage for storing codified electronic medical data. The data storage may include a database of predetermined study types. Each predetermined study type in the database may be associated with a set of conditions and parameters. The system may also include a computer unit for executing computer software to search the codified electronic medical data according to the weighted conditions and creating a pool of candidates. The system may also include a display unit for displaying the pool of candidates in order from the most optimal results to the least optimal results.

Certain embodiments of the present invention may include a computer readable medium having a set of instructions for execution by a computer. The instructions may include an input routine for receiving a plurality of conditions. The instructions may also include a ranking routine for ranking said plurality of conditions. The instructions may also include an identifying routine for identifying whether a specific condition is mandatory. The instructions may also include an assignment routine for optionally assigning a deviation for numerical ranges. The instructions may also include a search routine for searching codified electronic medical data to create a pool of candidates according to the conditions, the rank of the conditions, the designation as mandatory, and if present, a deviation for numerical ranges. The instructions may also include a display routine for displaying the pool of candidates in order from the most optimal results to the least optimal results. The instructions may also include a selection routine for selecting a sub-set of said pool of candidates to retrieve further information for said sub-set.

BRIEF DESCRIPTION OF SEVERAL VIEWS OF THE DRAWINGS

FIG. 8 illustrates an example of four conditions a user may input to create a pool of candidates.

FIG. 9 illustrates an embodiment of the invention wherein the user interface allows the end-user to assign a weight to the conditions used to create a pool.

FIG. 10 illustrates a user interface screen wherein the user interface is displaying the results of the pool created according to the parameters outlined in the example of FIG. 9.

FIG. 11 illustrates a flow diagram for a method for generating a pool of potential clinical study participants in accordance with an embodiment of the present invention.

FIG. 12 illustrates a flow diagram for a method for generating a pool of potential clinical study participants in accordance with an embodiment of the present invention.

Figure 1:
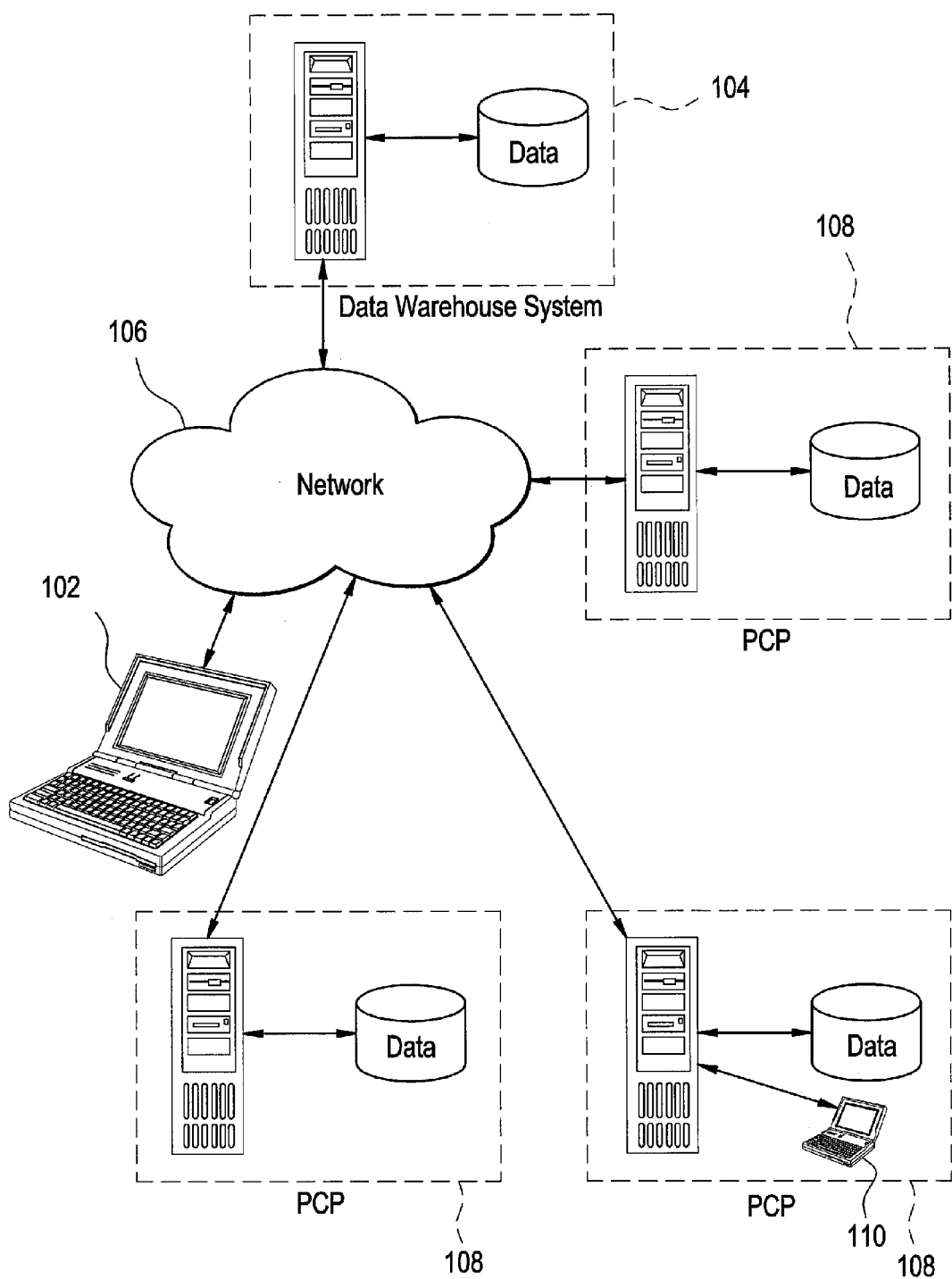
FIG. 1 is an exemplary system for securing patient identity in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments provide electronic medical record data which may, among other things, be searched to identify participants for one or more clinical studies. As used herein, clinical study may include one or more of clinical research studies on human patients (any phase), registry studies, studies to monitor special populations (elderly, pediatrics, other), and/or other clinically-based studies, for example. In many clinical studies, protecting patient identity, as defined by HIPAA, is an important concern. That is, patient information should be made available for use in clinical studies and other applications with the particular identity of that patient obscured for those not authorized under HIPAA.

Certain embodiments provide a secure process for sending de-identified patient information from an ambulatory patient care provider (PCP) site to a data warehouse system where the patient data may be analyzed and compared with a wider range of patient data. The terms "de-identified patient information" and "de-identified patient data" as used in this document refer to both fully de-identified data as defined by HIPAA and limited data set data as defined by HIPAA. A limited data set is protected health information for research, public health and health care operations that excludes direct identifiers (e.g., name; postal address other than city, state and zip code; social security number; medical records numbers) but in which other identifying information may remain (e.g., dates of examination; documentation; diagnosis; prescription; lab test results). This is contrasted with fully de-identified data as defined by HIPAA, where all data that may be used to trace back to an individual patient is removed from the record. Information obtained through the data warehouse that pertains to individual patients is transmitted back to the originating PCP site, via a cohort report. Cohort reports are generated by queries that are executed against the data warehouse system to identify patient cohort groups. The individual patients included in a cohort report are then re-identified at the PCP site so that the PCPs may consider the information when deciding on treatment options for the individual patients.

Alternatively and/or in addition, a cohort report may be used to send a list of patients and/or healthcare practitioners qualified for a particular clinical study back to the PCP. For example, a query representing a protocol of a clinical study is packaged and sent to a PCP or other site, such as a specialist or ancillary healthcare provider, to be processed by a host EMR application. A report is generated including a set of patients and may alert that one or more patient 'matches' exist. In certain embodiments, a cohort list may be routed using a variety of technologies and may be sent to a list of interested parties (e.g., a pharmaceutical company, contract research organization, other third-party, etc.).

FIG. 1 is an exemplary system for securing patient identity. PCP systems 108 located at various PCP sites are connected to a network 106. The PCP systems 108 send patient medical data to a data warehouse located on a data warehouse system 104. The PCP systems 108 typically include application software to perform data extraction along with one or more storage device for storing the electronic medical records (EMRs) associated with patients treated at the PCP site. In addition, the PCP systems 108 may include PCP user systems 110 to access the EMR data, to initiate the data extraction and to enter a password string to be used for encrypting a patient identifier. The PCP user systems 110 may be directly attached to the PCP system 108 or they may access the PCP system 108 via the network 106. Each PCP user system 110 may be implemented using a general-purpose computer executing a computer program for carrying out the processes described herein. The PCP user systems 110 may be personal computers or host attached terminals. If the PCP user systems 110 are personal computers, the processing described herein may be shared by a PCP user system 110 and a PCP system 108 by providing an applet to the PCP user system 110. The storage device located at the PCP system 108 may be implemented using a variety of devices for storing electronic information such as a file transfer protocol (FTP) server. It is understood that the storage device may be implemented using memory contained in the PCP system 108 or it may be a separate physical device. The storage device contains a variety of information including an EMR database.

In addition, the system of FIG. 1 includes one or more data warehouse user systems 102 through which an end-user may make a request to an application program on the data warehouse system 104 to access particular records stored in the data warehouse (e.g., to create a cohort report). In an exemplary embodiment of the present invention, end-users may include PCP staff members, pharmaceutical company research team members and personnel from companies that make medical and/or other products. The data warehouse user systems 102 may be directly connected to the data warehouse system 104 or they may be coupled to the data warehouse system 104 via the network 106. Each data warehouse user system 102 may be implemented using a general-purpose computer executing a computer program for carrying out the processes described herein. The data warehouse user systems 102 may be personal computers or host attached terminals. If the data warehouse user systems 102 are personal computers, the processing described herein may be shared by a data warehouse user system 102 and the data warehouse system 104 by providing an applet to the data warehouse user system 102.

The network 106 may be any type of known network including a local area network (LAN), a wide area network (WAN), an intranet, or a global network (e.g., Internet). A data warehouse user system 102 may be coupled to the data warehouse system 104 through multiple networks (e.g., intranet and Internet) so that not all data warehouse user systems 102 are required to be coupled to the data warehouse system 104 through the same network. Similarly, a PCP system 108 may be coupled to the data mining host system 104 through multiple networks (e.g., intranet and Internet) so that not all PCP systems 108 are required to be coupled to the data warehouse system 104 through the same network. One or more of the data warehouse user systems 102, the PCP systems 108 and the data warehouse system 104 may be connected to the network 106 in a wireless fashion and the network 106 may be a wireless network. In an exemplary embodiment, the network 106 is the Internet and each data warehouse user system 102 executes a user interface application to directly connect to the data warehouse system 104. In another embodiment, a data warehouse user system 102 may execute a web browser to contact the data warehouse system 104 through the network 106. Alternatively, a data warehouse user system 102 may be implemented using a device programmed primarily for accessing the network 106 such as WebTV.

The data warehouse system 104 may be implemented using a server operating in response to a computer program stored in a storage medium accessible by the server. The data warehouse system 104 may operate as a network server (often referred to as a web server) to communicate with the data warehouse user systems 102 and the PCP systems 108. The data warehouse system 104 handles sending and receiving information to and from data warehouse user systems 102 and PCP systems 108 and can perform associated tasks. The data warehouse system 104 may also include a firewall to prevent unauthorized access to the data warehouse system 104 and enforce any limitations on authorized access. For instance, an administrator may have access to the entire system and have authority to modify portions of the system and a PCP staff member may only have access to view a subset of the data warehouse records for particular patients. In an exemplary embodiment, the administrator has the ability to add new users, delete users and edit user privileges. The firewall may be implemented using conventional hardware and/or software as is known in the art. In certain embodiments, the data warehouse system 104 is implemented as a plurality of related and/or linked databases or data warehouses.

The data warehouse system 104 also operates as an application server. The data warehouse system 104 executes one or more application programs to provide access to the data repository located on the data warehouse system, as well as application programs to import patient data into a staging area and then into the data warehouse. In addition, the data warehouse system 104 may also execute one or more applications to create patient cohort reports and to send the patient cohort reports to the PCP systems 108. Processing may be shared by the data warehouse user system 102 and the data warehouse system 104 by providing an application (e.g., java applet) to the data warehouse user system 102. Alternatively, the data warehouse user system 102 can include a stand-alone software application for performing a portion of the processing described herein. Similarly, processing may be shared by the PCP system 102 and the data warehouse system 104 by providing an application to the PCP system 102 and alternatively, the PCP system 102 can include a stand-alone software application for performing a portion of the processing described herein. It is understood that separate servers may be used to implement the network server functions and the application server functions. Alternatively, the network server, firewall and the application server can be implemented by a single server executing computer programs to perform the requisite functions.

The storage device located at the data warehouse system 104 may be implemented using a variety of devices for storing electronic information such as a file transfer protocol (FTP) server. It is understood that the storage device may be implemented using memory contained in the data warehouse system 104 or it may be a separate physical device. The storage device contains a variety of information including a data warehouse containing patient medical data from one or more PCPs. The data warehouse system 104 may also operate as a database server and coordinate access to application data including data stored on the storage device. The data warehouse may be physically stored as a single database with access restricted based on user characteristics or it can be physically stored in a variety of databases including portions of the database on the data warehouse user systems 102 or the data warehouse system 104. In an exemplary embodiment, the data repository is implemented using a relational database system and the database system provides different views of the data to different end-users based on end-user characteristics.

Figure 2:
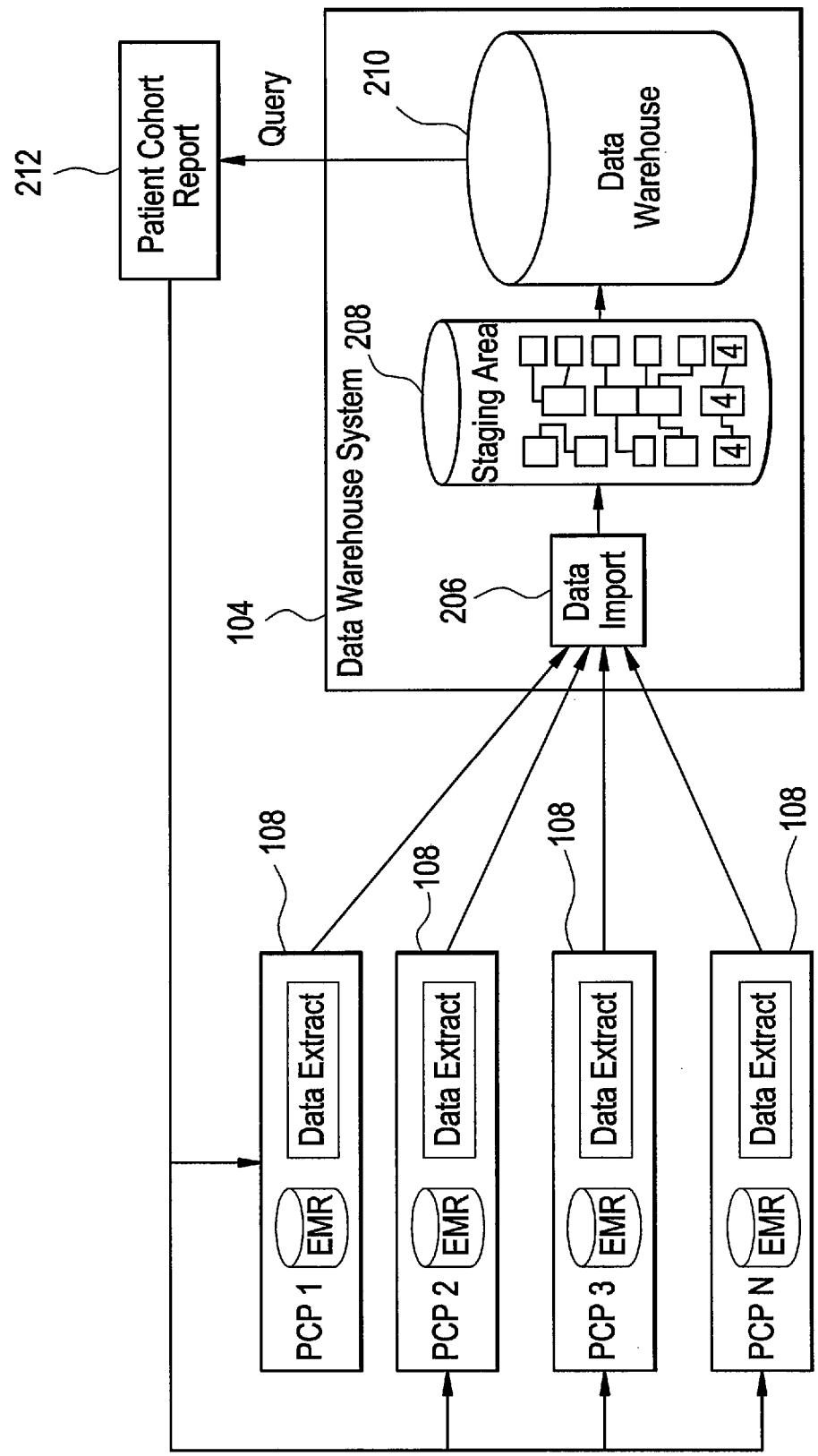
FIG. 2 is a block diagram of an exemplary data warehouse architecture in accordance with an embodiment of the present invention.

FIG. 2 is a block diagram of an exemplary data warehouse architecture. Patient data is extracted from EMR databases located in the PCP systems 108. In an exemplary embodiment of the present invention, an EMR database record includes data such as: patient name and address, medications, allergies, observations, diagnoses, and health insurance information. The PCP systems 108 include application software for extracting patient data from the EMR database. The data is then de-identified and transported (e.g., via Hypertext Transfer Protocol (HTTP) or Secure HTTP (HTTPS)) over the network 106 to the data warehouse system 104. In certain embodiments, the data warehouse system 104 may be implemented as a plurality of data warehouses and/or databases, for example. The data warehouse system 104 includes application software to perform a data import function 206. The data import function 206 aggregates and cleanses de-identified patient data from multiple sites and then stores the data into a staging area 208. Data received from multiple PCP systems 108 is normalized, checked for validity and completeness, and either corrected or flagged as defective. Data from multiple PCP systems 108 is then combined together into a relational database. Aggregation, cleaning and staging data in the described fashion allows the data to be queried meaningfully and efficiently, either as a single entity or specific to each individual PCP site 108. The de-identified patient data is then staged into a data warehouse 210 where it is available for querying.

Patient cohort reports 212 are generated by application software located on the data warehouse system 104 and returned to the PCP systems 108 for use by the primary care providers in treating individual patients. Patient cohort reports 212 may be automatically generated by executing a canned query on a periodic basis. PCP staff members, pharmaceutical company research team members and personnel from companies that make medical and/or other products may each run patient cohort reports 212. In addition, patient cohort reports 212 may be created by an end-user accessing a data warehouse user system 102 to create custom reports or to initiate the running of canned reports. Further, patient cohort reports 212 may be automatically generated in response to the application software, located on the data warehouse system 104, determining that particular combinations of data for a patient are stored in the data warehouse. An exemplary patient cohort report 212 includes all patients with a particular disease that were treated with a particular medication. Another exemplary patient cohort report 212 includes patients of a particular age and sex who have particular test results. For example, a patient cohort report 212 may list all women with heart disease who are taking a hormone replacement therapy drug. The patient cohort report 212 would list all the patients with records in the data warehouse 210 that fit this criteria along with a warning about the possible side-effects and the likelihood of the side-effects occurring. In an exemplary embodiment, each PCP site receives the entire report, in another embodiment, each PCP site receives the report only for patients that are being treated at the PCP site.

Figure 3:
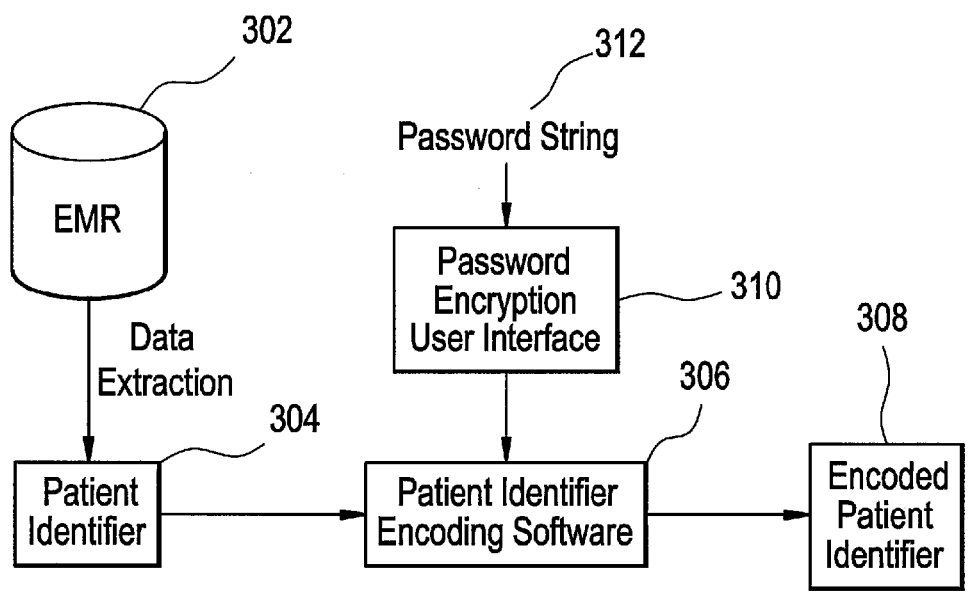
FIG. 3 depicts an exemplary process for de-identifying patient data for storage in a data warehouse used in accordance with an embodiment of the present invention.
Figure 4:
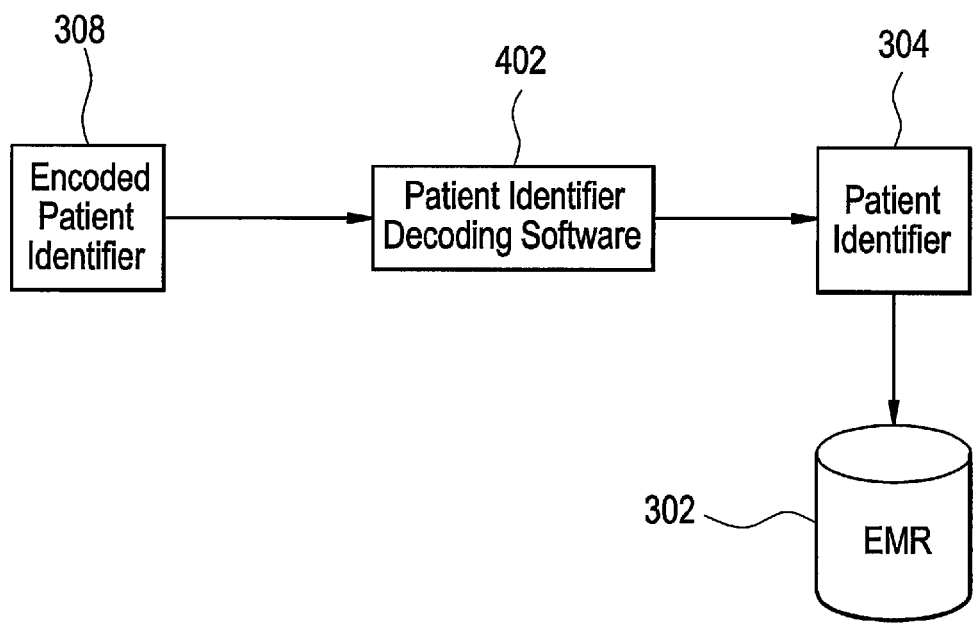
FIG. 4 is a block diagram of an exemplary process for re-identifying a patient from de-identified patient data in accordance with an embodiment of the present invention.

In an exemplary embodiment of the present invention, the ability to create patient cohort reports 212 based on querying longitudinal patient data is supported by the ability to connect all records relating to a single patient in the data warehouse 210. This requires a unique identifier to be associated with each patient record that is transmitted to the data warehouse 210. The unique identifier indicates an anonymous or abstract patient having certain characteristics but does not provide directly identifying information such as name, social security number, street address, etc. However, individual PCPs may want to retain the ability to re-identify a patient based on the unique identifier so that the medical personnel located at the PCP site can follow through with the patient in response to information included in the patient cohort reports 212. FIG. 3 depicts an exemplary process for de-identifying patient data for storage in a data warehouse 210 located at the data warehouse system 104 and FIG. 4 depicts an exemplary process for re-identifying a patient from the de-identified patient data contained in a patient cohort report 212.

FIG. 3 is a block diagram of an exemplary process for de-identifying patient data during data extraction for transmission to a data warehouse system 104. The de-identification process removes information that will identify a patient while still retaining clinically useful information about the patient. Patient data is extracted from the EMR database 302 and identifying information is removed, resulting in de-identified patient data. In an exemplary embodiment of the present invention, an EMR database 302 includes the following patient identifying demographic data: names; geographic identifiers, including address; dates directly related to an individual, including birth date, admission date, discharge date and date of death; telephone and fax numbers; electronic mail addresses; social security number; medical record number; health plan beneficiary; account numbers; certificate or license numbers; vehicle identifiers and serial numbers including license plate numbers; device identifiers and serial numbers, web Universal Resource Locators (URLs) and internet protocol (IP) address numbers; biometric identifiers, including finger and voice prints; full face photographic images and comparable images; other unique identifying numbers, characteristics and codes assigned by the PCP or by the EMR system for administrative purposes, including a patient identifier (PID) 304. The EMR database 302 also includes information about: the patient diagnosis or problem; medications taken or prescribed; observations, diagnostic laboratory tests and vital signs; subjective and objective findings, assessments, orders, plans, and notes documented by healthcare providers. The EMR database 302 also includes audit information that records the date, time, and identity of persons who have created, read, updated, or deleted information from the patient record. The EMR database 302 record for each patient also contains a numeric key known as the PID 304 which may be used to uniquely identify an individual patient. The PID 304 is encoded as part of the de-identification process to create an encoded patient identifier (EPID) 308. The EPID 308 is sent, along with the de-identified patient data, to the data warehouse system 104.

The extraction process is performed by application software located on the PCP system 108 and may be executed in the background on a periodic basis (e.g., at 2 a.m. every night, at 2 a.m. every Saturday). In this manner, the extraction process will be less likely to interfere with existing software located on the PCP system 108. The extraction process may also be initiated by a remote system (e.g., the data warehouse system 104) and may include fall or incremental back-up schemes. In an exemplary embodiment of the present invention, the following identifiers are removed or transformed in order to create de-identified data that would be classified under the HIPAA definition as fully de-identified data: name, geographic subdivisions smaller than a state including street address, city, county, precinct, zip code (down to the last three digits), dates directly related to an individual (e.g., birth date), phone and fax numbers, electronic mail addresses, health plan number, account number, certificate/license number, device identifier and serial numbers, unified resource locator (URL), internet protocol (IP) address, biometric identifiers, fall face photograph, and other unique identifying numbers, characteristics or codes.

In certain embodiments, the extraction process may be initiated remotely. In certain embodiments, the extraction process may be implemented as a software 'bot' or other packaged application that is sent to an end-user and deployed on an individual client or enterprise-wide server, for example.

In an alternate exemplary embodiment of the present invention, the following identifiers are removed or transformed in order to create de-identified data that would be classified under the HIPAA definition as limited data set information: direct identifiers such as name, postal address (other than city, state and zip code), social security number and medical records numbers. In the limited data set information implementation of the present invention some identifying information may remain such as dates of examination, documentation, diagnosis, prescription and lab test results.

A novel EPID 308 is assigned to each patient based on the PID 304 associated with the patient and a password entered by the PCP. The PID 304 to EPID 308 mapping is not maintained persistently. As depicted in the exemplary embodiment shown in FIG. 3, a password string 312 is supplied by the PCP via a password encryption user interface 310 on the PCP user system 110. This password string 312 is known only to the PCP and is required in order to decode the EPID 308 into a PID 304. The user at the PCP site must have the password string 312 to obtain the PID 304 and this password string 312 must be re-entered each time a patient is to be re-identified. The password encryption user interface 310 may be a graphical user interface. In an exemplary embodiment of the present invention, the user entered password string 312 is encoded using the two-fish algorithm. The two-fish algorithm, as known in the art, is a secret-key block cipher cryptography algorithm that is designed to be highly secure and highly flexible. It utilizes a single key for both encryption and decryption and is often referred to as symmetric encryption. The encoding is performed by patient identifier encoding software 306 located on the PCP system 108. The patient identifier encoding software 306 also hashes the encoded password string to produce a sixteen-digit number. This sixteen-digit number is numerically added to the PID 304 to create the EPID 308. Other methods of creating the EPID 308 from the PHD 304 may be utilized with an exemplary embodiment of the present invention (e.g. Rivest, Shamir and Adelman, RSA, algorithm based on patient name, age and social security number, etc.) as long as the EPID may only be decoded at the PCP site.

FIG. 4 is a block diagram of an exemplary process for re-identifying a patient from de-identified patient data. As described previously, population cohort reports 212 of at-risk patients are created by running queries against the data warehouse 210. De-identified individuals may be tracked longitudinally and queried as members of anonymous population cohorts, based on clinical selection criteria. The query result, contained in the cohort report 212, is a list of EPIDs 308. A list of patient EPIDs 308 in a patient cohort report 212 are received by the PCP system 108. The EPIDs 308 are read into the patient identifier decoding software 402, located on the PCP system 108, and the original PID 304 is recreated or otherwise re-associated with a patient record at the PCP system 108. The PID 304 may be used as a key to look up additional identifying information from the EMR database 302. Employees of the PCP may utilize the patient-specific information from the EMR database 302 to counsel the patient and to decide on treatment alternatives.

An embodiment of the present invention allows for ambulatory PCPs to send patient data into a data warehouse containing patient data from other ambulatory PCPs. In this manner, patient data may be analyzed and compared to a larger population of patients. The de-identified patient data includes an EPID 308 that may be useful in creating longitudinal reports that analyze more than one record for a particular patient. The effects of certain drugs and treatments on patient cohort groups can be analyzed and may lead to improvements in the use or composition of the drugs and treatments. In addition, an embodiment of the present invention allows for the PCP to receive cohort reports 212 based on data contained in the data warehouse. These patient cohort reports 212 include an EPID 308 for each patient. The EPID 308 may be decoded at the PCP site that created the EPID 308 and used to identify a particular patient. In this manner a PCP, by considering the information contained in the cohort report, may be able to provide improved treatment to the patient. This ability to provide useful information back to a patient level may also lead more PCPs to participate in sending patient data to a data warehouse. Having more data in the data warehouse may provide more useful information to third parties such as pharmaceutical companies, medical device companies and physicians about the effects and risks of particular treatments, while minimizing the risk of disclosing patient-identifying information to third parties. This may lead to improvements in preventative care as well as other types of medical care.

As described above, the embodiments of the invention may be embodied in the form of computer-implemented processes and apparatuses for practicing those processes. Embodiments of the invention may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. An embodiment of the present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

In certain embodiments, once patient information is re-identified, the user may send the corresponding list of patients into EMR as an inquiry for further analysis, manipulation, etc. A re-identified patient record may be modified, compared, and/or otherwise manipulated by the authorized user and saved locally and/or in an EMR database or other storage. A modified record may be de-identified before is it saved, for example.

In certain embodiments, EMR updates are "pulled", "pushed", or otherwise communicated to a database, data warehouse and/or other data store on a periodic basis (e.g., nightly, weekly, etc.). In certain embodiments, changes made locally to re-identified patient records are de-identified and communicated to the EMR system and/or database for storage.

In certain embodiments, a user may search for one or more patient records within EMR by invoking a "find" dialog or search function. The user may search by the EPID, for example, and enter or select an EPID number to activate a search. The corresponding patient chart may be retrieved and displayed. Thus, a patient may be re-identified for an authorized healthcare provider who has been identified and verified.

Thus, de-identification and re-identification enable encoded and unencoded data to work in physically separated systems together. Whereas the encrypted system may host patient-level information that's HIPAA compliant and provide features that are useful from an encrypted point of view (e.g. provide data views to a larger audience, etc.), a need exists to leverage the information from the encrypted system and to re-identify the information for those audiences who are physically separated from the encrypted system but who have the authorization to view patient identifiable information. The process of re-identifying the patients is a process that occurs, for example, on the local system.

In certain embodiments, separation of de-identified and identified patient data facilitates broader analysis of patient populations without breaching individual patient security. Population-based analysis may be performed safely while maintaining patient privacy. Re-identification may occur at the local system level to allow a patient's healthcare provider to diagnose, treat and/or provide other services to the patient.

Thus, broader analysis of patient information may be allowed while at the same time respecting patient privacy. Communities of health care providers may benchmark, and compare patient populations without compromising patient privacy. At the same time, a patient's provider may re-identify patients from within the patient populations at the local level that are hosted/presented by the encrypted site. Re-identification algorithms may be stored locally at the healthcare provider level, for example. This physical separation may limit a potential risk of other providers who are viewing de-identified data on a portal from viewing patient identifiable information.

Certain embodiments allow for patient information to be shared with interested parties without compromising patient privacy. In the broader healthcare space, there will be applications where researchers, government agencies, communities of practice, may want to study patient populations but are, as of now, restricted because no good mechanism exists to work with source data providers in de-identifying and re-identifying patients. Certain embodiments facilitate such interaction. For example, decrypted information may be re-identified and then consumed by or imported into a patient's provider system within Excel, Centricity Physician Office EMR application and/or other application. Other entities, such as researchers and agencies, may view and/or manipulate the encrypted or de-identified data with reduced risk of compromising patient privacy.

Figure 5:
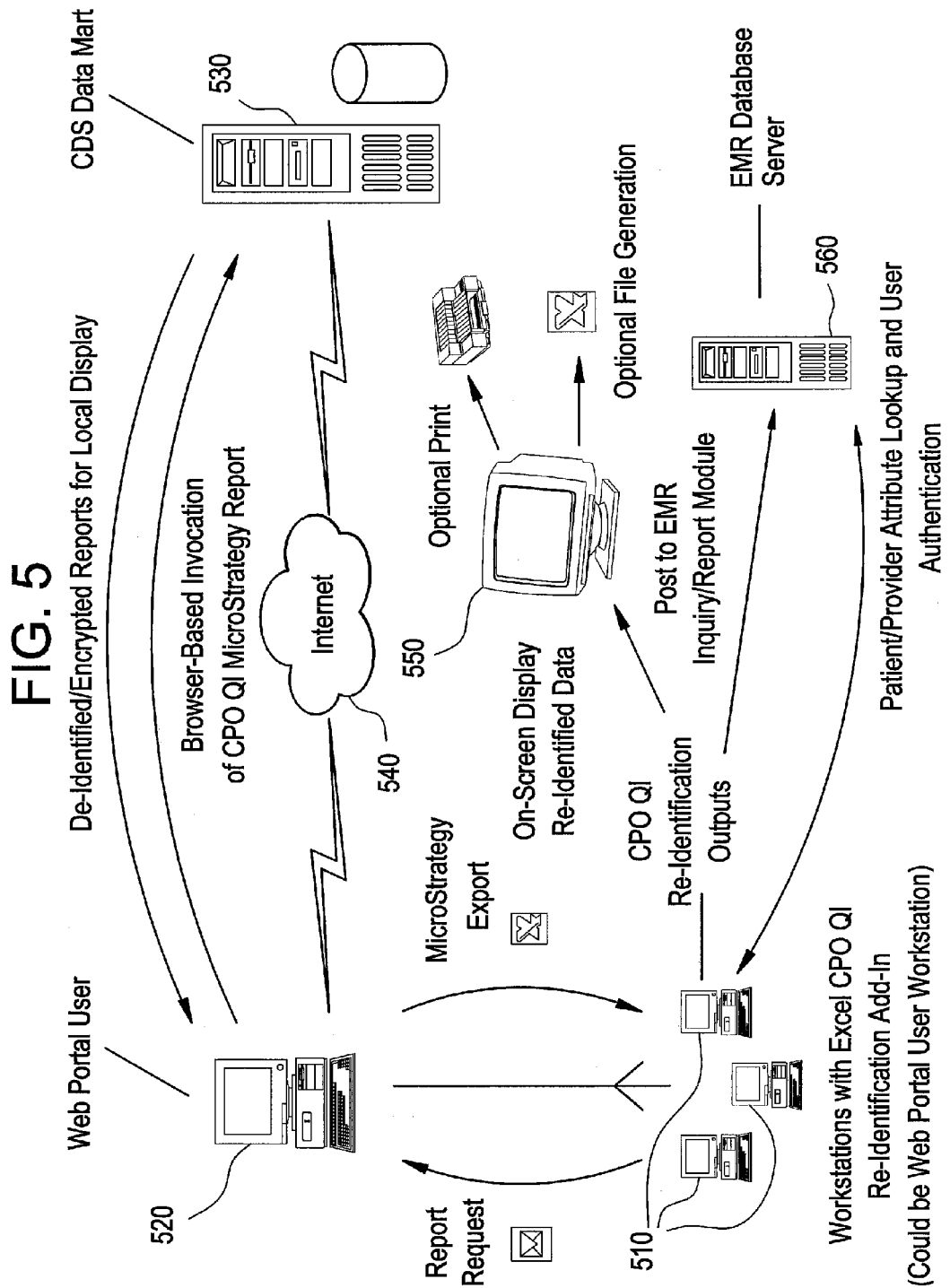
FIG. 5 illustrates a system for patient data de-identification and re-identification in accordance with an embodiment of the present invention.

FIG. 5 illustrates a system 500 for patient data de-identification and re-identification in accordance with an embodiment of the present invention. The system 500 includes one or more user workstations 510, a web portal 520, a data store 530 and a data link 540. The system 500 may also include a display 550 and/or a data server 560, for example.

The components of the system 500 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain components may be integrated in various forms and/or may be provided as software and/or other functionality on a computing device, such as a computer. Certain embodiments may omit one or more of the components of the system 500 to execute the re-identification and/or de-identification functions and communicate data between a local user and a data store.

In operation, the workstation 510 may request data via the web portal 520. For example, a user at the workstation 510 requests patient-related data via a web browser that accesses the web portal 520. The web portal 520 communicates with the data store 530 via a data link 540. For example, the web portal 520 requests the data from the data store 530, such as from an EMR data mart, via a network, such as the Internet or a private network. The data store 530 returns the requested data to the workstation 510 via the web portal 520. The data may include non-HIPAA-protected data, de-identified/encrypted patient data, re-identified patient data, and/or other data, for example.

The user workstation 510 may communicate with the display 550 to display data transmitted from the data store 530. Data may also be printed and/or used to generate a file, for example. The workstation 510 may also communicate with the data server 560 to transmit the data and/or other update, for example.

In certain embodiments, a de-identified patient report is transmitted to the workstation 510 from the data store 530 via the web portal 520 in response to a request from the workstation 510. The workstation 510 performs a re-identification of the de-identified patient data locally at the workstation 510. The re-identification may be performed via lookup of an EPID to determine a corresponding PID or other similar technique, for example. The re-identification functionality may be integrated into a document viewing/editing program, such as Microsoft Excel, Microsoft Word, and/or other software, for example. The re-identification function may access data in an external source, such as the data store 530 and/or the data server 560, to match the EPID to the PID. In certain embodiments, the EPID is replaced with the PID and/or other patient identifying information (e.g., patient name) in a document at the workstation 510.

In certain embodiments, the workstation 510 may first authenticate a privilege or right of access via the server 560, for example, before the patient data is re-identified. The workstation 510 may also lookup patient and/or provider attributes via the server 560 and/or data store 530, for example.

In certain embodiments, information in electronic medical reports and/or other documents may be processed to normalize or "scrub" the information according to a particular lexicon and/or grammar. For example, a medical report table, such as a Logician® medical data table, may include one or more observation values from an examining physician or other medical professional. The observation value (e.g., "obs" or "obsvalue") field may be a free-format field, for example. Thus, different physicians may use different language to refer to the same condition. For example, one physician may refer to a heart attack while another may refer to an acute myocardial infarction. Terms may be "scrubbed" or parsed and associated with a numeric value and/or "standard" term for a lexicon/grammar.

For example, information in an electronic medical record or other document may be processed by a data processing system prior to storage in a data warehouse or other data collection. The information may be matched, based on one or more rules, for example, to a table or other listing of accepted terms/values. Based on the matching, the information may be replaced with the accepted term and/or value from the listing.

Using the example above, if the accepted term was "acute MI", a physician's use of "heart attack" would be converted or normalized to "acute MI" and a physician's use of "acute myocardial infarction" would also be converted to "acute MI."

In certain embodiments, certain identified patient data is extracted and stored centrally in a large data warehouse. During storage, the data may be scrubbed and normalized by mapping terms to a common vocabulary and/or set of rules. For example, if one record refers to a MI and another record refers to a myocardial infarction, both are coded centrally in the database as a myocardial infarct. Thus, a search of records in the database may be executed based on the common vocabulary.

A user may execute a search using one or more terms or criteria for the search. For example, a user may request a pool of patients over the age of 55, with a history of acute myocardial infarction within the last 2 years, and certain enzyme levels, who live in the Midwest. The terms and/or criteria may already be codified in the database and/or may be codified/normalized upon entry of the search terms by the user, for example. In certain embodiments, a user may select one or more codified terms from a menu or other listing and select one or more predesigned algorithms to search for patients meeting the selected term(s). In certain embodiments, a user may codify additional term(s) and/or create additional rules/search algorithms dynamically, for example. In certain embodiments, a search system accommodates a user's query to codify language used in the query to a standard vocabulary or set of allowed terms. A search having multiple criteria may progress by applying the plurality of criteria in succession to narrow the pool of candidates. Search terms may be matched to electronic medical records and/or other entries in a data warehouse and/or other database, for example.

In certain embodiments, electronic medical record data may be centralized and codified. In certain embodiments, electronic medical record data may be distributed and/or uncodified. In certain embodiments, electronic medical record data may be codified differently in different systems. For example, a local vocabulary may be different from a centralized vocabulary and/or different local EMR systems may have different local vocabularies. In certain embodiments, a mapping may exist between a plurality of codifications to allow conversion and searching between the different codification schemes.

Terms or input by a user may be codified according to a diagnostic code such as an ICD-9 (International Classification of Diseases, Ninth Revision) code, ICD-10 code or a CPT (Current Procedure Terminology) code, for example. Alternatively and/or in addition, terms may be codified according to a proprietary terminology or coding schema. For example, an industry standard term such as "acute, upper right extremity pain" may be classified as "acute, upper right arm pain." Certain terms may be classified or replaced by commonly used terms and/or terms appropriate for a particular environment or application, for example. In certain embodiments, a user may select a term, and a master vocabulary table returns relevant terms for use in searching. In certain embodiments, one or more categories may be searched base on a clinical condition or a disease category, for example.

For example, if a user wishes to search for a "CV" (cardiovascular) issue, the user may select a number of CV conditions from a CV list. For example, a search interface may have clinical conditions listed, such as a person who had a heart attack with complications from diabetes, and the interface may have diagnostic codes listed for selection to search. A user may then search on either or both of the clinical conditions and codes by selecting conditions/codes from a flat or tiered listing or menu and/or by manually entering conditions/codes to select the clinical conditions and/or other criteria to be used to be applied to the database and search.

According to one of the examples above, a user selects the following criteria for searching: age exceeding 55, acute myocardial infarction, within a time frame of 2 years, a certain specified enzyme level or range of levels, and a geographic location of "the Midwest". A search would identify patients in the database over 55 years of age. The search would narrow that group by identifying those patients in the over 55 age group having an acute myocardial infarction within the last two years. Additionally, the search would narrow the group of patients to isolate patients over 55 who have had an acute myocardial infarction in the last two years who reside in the Midwest. The result is a pool of potential study participants satisfying the criteria supplied by a user. Study participants may include clinical study subjects (e.g., patients) and/or clinical study investigators (e.g., physicians and/or other practitioners), for example.

Figure 6:
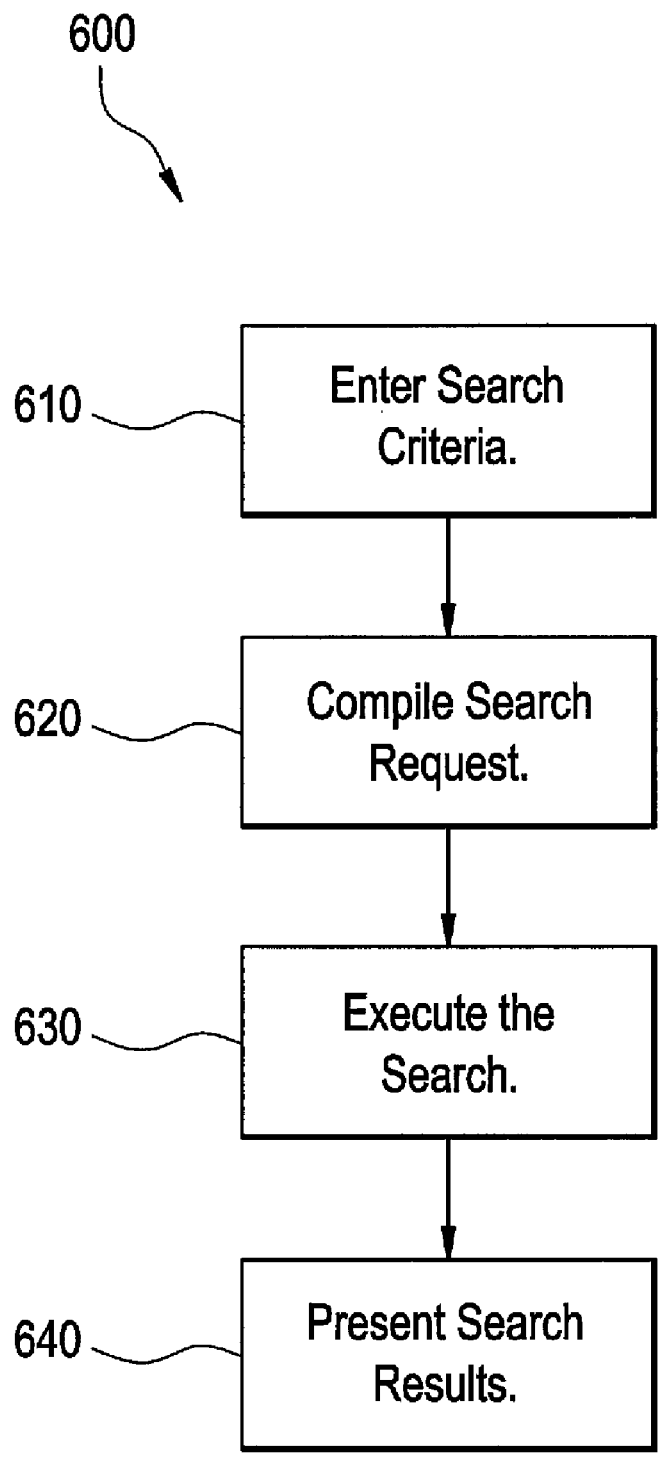
FIG. 6 illustrates a flow diagram for a method for generating a candidate pool from electronic medical records in accordance with an embodiment of the present invention.

FIG. 6 illustrates a flow diagram for a method 600 for generating a participant pool from electronic medical records in accordance with an embodiment of the present invention. At step 610, one or more search criteria are entered. For example, a user, such as a physician or pharmaceutical researcher, may manually enter one or more search terms/criteria. A user may manually enter and/or select criteria according to one or more preconfigured vocabularies and/or sets of codes, for example. Alternatively and/or in addition, a user may enter search criteria which is then normalized or codified in accordance with a vocabulary, for example. In certain embodiments, search criteria may be selected from a single- or multi-tiered menu and/or other listing instead of and/or in addition to manual entry by a user.

At step 620, a search request is compiled for an electronic medical records database or other data storage. For example, a plurality of search criteria/terms entered and/or otherwise selected by a user are organized into a request or query for electronic medical record storage. In certain embodiments, compilation or organization of a search request may involve normalization or codification of search criteria according to a certain standard or approved vocabulary or list of terms, for example.

At step 630, a search is executed to identify each of the search criteria in the electronic medical record data. For example, a pool of potential study participants may be identified from a database, data warehouse and/or other data store of electronic medical record data based on the search criteria. Each of the search criteria may further narrow the pool to arrive at a desired set of participants.

At step 640, search results are presented. Search results may be de-identified and/or re-identified, as described above. Search results may include varying degrees of information. Search results may be further refined and/or prioritized, for example. In certain embodiments, search results may be routed and/or transferred to another application, such as a notification application, for example. Search results may be displayed, formatted, printed, electronically mailed, transmitted via facsimile and/or other transmission and/or storage, for example.

One or more of the steps of the method 600 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 7:
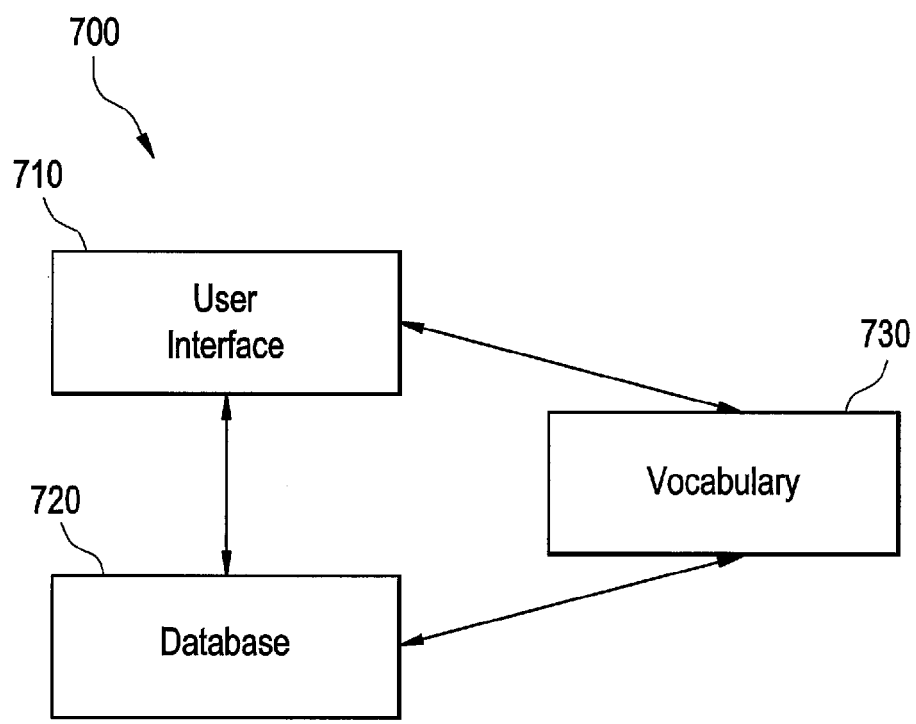
FIG. 7 illustrates an electronic medical records search system 700 used in accordance with an embodiment of the present invention.

FIG. 7 illustrates an electronic medical records search system 700 used in accordance with an embodiment of the present invention. The system 700 includes a user interface 710, a database 720, and a vocabulary 730. Similar to embodiments described above, a user may access the user interface 710 to execute a search to identify a potential pool of participants. In certain embodiments, the system 700 may be similar to the system(s) described above with respect to FIGS. 1 and 5, for example.

The user may enter one or more terms and/or select one or more terms from a menu or other single- or multi-tiered list(s), for example. Term(s) may be selected and/or entered according to one or more predetermined and/or standard vocabulary(ies), lexicon(s), grammar(s), code(s), etc., such as vocabulary 730. Alternatively, term(s) may be selected and/or entered without regard to a particular vocabulary, lexicon, grammar and/or code and then normalized and/or otherwise converted according to a vocabulary, lexicon, grammar, code and/or list of terms. In certain embodiments, term(s) and/or other criteria may be entered and utilized for a search without normalization or other conversion.

Term(s) from the vocabulary 730 and/or other search terms/criteria may be used to query the database 720 and/or other data store including electronic patient medical information. As described above, one or more terms/criteria may be used to identify patients in the database 720 satisfying the criteria and/or including the terms. For example, a database search algorithm, custom search routine and/or other search may be executed with respect to the database 720 to identify relevant patient data. A search may be an iterative search applying each of the supplied criteria in succession until a desired pool of potential participants is identified. Search results may then be output via the user interface 710 for use by the user.

The components of the system 700 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain components may be integrated in various forms and/or may be provided as software and/or other functionality on a computing device, such as a computer. Certain embodiments may omit one or more of the components of the system 700 to identify a pool of potential participants for clinical study or trial.

In the software method described above for creating a pool of potential study participants, each of the conditions is equally weighted. For example, if an end-user inputs a list of four conditions that the members of the pool should have, a pool of participants having those four conditions is generally returned.

For illustration, FIG. 8 is an example of four conditions a user may input to create a pool of participants. FIG. 8 is for illustration only and more or less conditions, different from the conditions illustrated, may be used with an embodiment of the invention. As shown in FIG. 8, a user may input the following conditions: diabetes, family history of coronary artery disease, age equal to 25-30, and a geography of Illinois. Software may search a database and return a pool of participants having each condition. In the illustrative example of FIG. 8, only participants having diabetes, a family history of coronary artery disease, age equal to 25-30, and a geography of Illinois will be returned.

The pool of participants returned by the above described algorithm, however, may be unnecessarily restrictive. The algorithm may eliminate participants that do not precisely match the conditions as entered, but still may be satisfactory for the study. Accordingly, in order to maximize the size of a potential pool, it is desirable to allow a user to input a less rigorous set of conditions as opposed to examining whether the conditions exist or whether the conditions do not exist. One technique for allowing a user to input a less rigorous set of conditions may be allowing a user to weight the conditions. In other words, it is desirable to allow a user to identify conditions based on importance to a particular study.

In an embodiment of the present invention, a software algorithm utilizes a weight assigned to each condition to create a maximum size pool from a collection of codified electronic medical patient records. The weighting of each condition allows the software to perform a refining function for returning a more refined pool of participants.

In an embodiment, the user interface for the software algorithm allows the end-user to input a list of clinical conditions. The clinical conditions may be identifiable and tied in with the database to codified terms in the electronic medical patient records. The software algorithm may allow the end user to rank each condition by relative importance, and identify whether the condition is mandatory for the pool. The software algorithm may also allow the end user to assign a percentage deviation for numerical range conditions. Once the user has inputted the tailored conditions, the software algorithm may then perform a refinement function for creating the maximum total patient yield according to the weighting of each condition as assigned by the user. After the search is concluded, the software algorithm returns the results and displays a pool of potential participants. The software algorithm may allow the end user to select or de-select study parameters that have a high correlation with larger total patient yield.

FIG. 9 illustrates an embodiment of the invention wherein the user interface may allow the end-user to assign a weight to each of the conditions used to create the pool. FIG. 9 is for illustration only and more or less conditions, different from the conditions illustrated, may be used with an embodiment of the invention.

As shown in FIG. 9, the condition column 910 may be populated by a user inputting the conditions. The conditions may generally be identifiable by the database and tied to the codified terms in the electronic medical patient records. Additionally, in an embodiment, the condition column 910 may be populated by a user inputting a predetermined study type 915, and the associated conditions for that study type automatically populating the conditions column 910. For example, a user may input a predetermined study type 915 of Study A. The study type of Study A may be linked with a predetermined set of conditions that populate the conditions column 910. In an embodiment, the Study A may also be linked with the other parameters such as, ranking, percentage deviation, and whether the condition is mandatory. In a similar manner, a Study B may be linked with a predetermined set of conditions, different from Study A, that may populate the conditions column 910. Any number of predetermined study types 915 may be used. Although only three parameters are illustrated in FIG. 9, more or less parameters may be utilized with embodiments of the invention. It is contemplated that some combination of user input and automatic population of the conditions column 910 may be utilized with embodiments of the present invention.

Study types may have associated search or variable parameters attached as defaults may include geography, patient volume, disease or therapeutic category. Study type defaults may be engaged when each respective study is chosen as the primary goal, focus or objective for a researcher. That is, searches may be optimized using default parameters as focused objectives. Searches may be optimized for focused objectives. For example, mandatory conditions may be applied to certain locations in a geography default, whereas other data elements may be optional, or weighted less. These defaults can create consistency in search methodology across data warehouses or sponsor organizations, for example.

In the example as shown in FIG. 9, a user may input the following conditions in the conditions column 910: diabetes, family history of coronary artery disease, age equal to 25-30, and a geography of Illinois. In the example as illustrated in FIG. 10, if these four conditions were entered into the user interface, the software algorithm would generally return a pool wherein each patient satisfied each condition. In the example as shown in FIG. 9, the conditions for the pool are one of several factors the software algorithm may use to tailor the creation of a pool of participants to obtain an improved amount of qualified participants for a particular study.

Once the user enters the conditions into conditions column 910, a user may input other information about the conditions to tailor the creation of the pool. As shown in FIG. 9, a user may rank each condition in rank column 920. A user may rank each condition by importance for the pool. For example, in FIG. 9, a user has ranked diabetes as the most important condition for the desired pool. The second most desired condition is a family history of coronary artery disease. The next most important condition is age. Finally, the least important condition is the geography of the participant.

The significance of the rankings of the conditions may be adjusted according to the whether the condition is mandatory for the pool. If a condition is mandatory, then a participant must satisfy the condition to be considered as for inclusion in the pool. If a condition is not mandatory, or optional, the condition is considered preferred. Participants not satisfying the condition, however, may be included in the pool. In the example as shown in FIG. 9, in column 940 a user may indicate whether the condition is mandatory for the pool. As shown in column 940, the user has indicated that conditions ranked 1 and 2 are mandatory for the study. In the example provided, the user has indicated that each member of the pool have diabetes and a family history of coronary artery disease. The user has indicated that the condition ranked 3, age equal to 25-30 and condition ranked 4, geography equal to Illinois, are not mandatory. These conditions, however, are preferred.

For conditions having a numerical value, such as condition 3 of FIG. 9 indicating age equal to 25-30, a user may designate an acceptable deviation. For example, in column 930, the user has indicated that a 10% deviation in age is acceptable for the desired pool. In this example, 10% of 25 is 2.5 years and 10% of 30 is 3 years. In an embodiment, software may accommodate a percentage or an absolute (integer or non-integer) deviation. In an embodiment, the software may round up to the nearest whole year. In the example of FIG. 9, the software may interpret the deviation to be 3 years. The significance of the level of deviation is adjustable by the user. A user may indicate that the numerical range of 25-30 is optimal, but a deviation of 3 years outside of the age range, 22-33 is acceptable. In an embodiment, the software may treat the age range with deviation limits as a mandatory condition. In this case, the software may treat the age range as 22-33 as a mandatory condition and not return any participants outside this age range. Alternatively, the software may treat the age range with deviation limits as optional. In such an embodiment, the age range 22-33 may be interpreted as preferred, but participants outside the age range may still be included in the pool. The numerical values as provided are for illustrative purposes only. Any numerical values may be used, including lab results or other numerical values from tests or other procedures.

As the parameters are currently set in FIG. 9, participants eligible for the pool must have diabetes and a family history of coronary artery disease. Any participants meeting these two conditions will be included in the pool. Optimal participants for the pool will meet the additional conditions, being between the ages of 25-30 and having a geography equal to Illinois. The next set of participants may meet conditions 1, 2, and 4 and be between the acceptable numerical deviation of condition 3. The next set of participants may meet conditions 1, 2, and 3 but not condition 4. The next set of participants may meet conditions 1, 2, and 4, but not condition 3. The next set of participants may meet only conditions 1 and 2. In such a manner, the participants are ranked according to their fit for the pool. For participants whose rankings turn on numerical values, the participants may be displayed according to the lesser amount of deviation from the optimal or desired numerical value. For example, participants whose ranking depends on their age in the above example, a participant of age 31 will be ranked ahead of a participant of age 19.

FIG. 10 continues the example of FIG. 9 illustrating a user interface screen wherein the user interface is displaying the results of the pool created according to the parameters outlined in the example of FIG. 9. In the first row of FIG. 10, the conditions are shown according to rank. Column 1010 lists all the participants A-I that satisfy the above parameters. The participants are listed in the optimal or more refined order according to the parameters. Columns 1020 and 1030 illustrate that the mandatory conditions are satisfied for each participant. Column 1040 lists the desired numerical value for each of the participants, in this case each participant's age. Column 1050 lists the geography of each participant.

As shown in FIG. 10, participants A-C are more optimal participants because they meet all four conditions. Participants D-E meets conditions 1, 2, and 4 and is within the acceptable range of deviation for condition 3. Participant F meets conditions 1, 2, and 3 but not condition 4. Participant G meets conditions 1, 2, and 4, but not condition 3. Participants H and I meet only conditions 1 and 2. The ranking algorithm as shown here is only an example. A user may adjust the ranking order and other ranking orders may be used. Alternatively or in addition, a deviation between a participant's actual geography and a desired geography may be identified. Deviation on a variable such as geography may be assessed by distance from a specific address or zip code. In an embodiment, a user may click on a patient to obtain further contact information or view the patient's medical records and/or history. Alternatively, the contact information may be displayed for a user. In yet another alternative, check boxes may be available for a user to select a subset of patients. The software may then retrieve the contact information and/or medical records and/or history for the selected patients. Additionally, in an embodiment, candidates that are optimal (A-C in the above example) and meet all the desired conditions may be highlighted or shaded to distinguish from the other candidates.

FIG. 11 illustrates a method 1100 in accordance with an embodiment of the present invention. At step 1110, a plurality of clinical conditions are received at a user interface. The conditions may generally be tied to codified terms in electronic medical patient records. At step 1120, parameters for tailoring a search of electronic medical records for the clinical conditions may be received. For example, such parameters may include ranking the conditions, determining whether the conditions are mandatory for the pool, and determining a percentage deviation for numerical ranges. At step 1130, an optimization function is executed to create a pool according to the specified conditions and parameters. At step 1140, the pool is displayed in an order from the most optimal results to the least optimal results.

FIG. 12 illustrates a method 1200 in accordance with an embodiment of the present invention. At step 1210, a user may input a plurality of clinical conditions at a user interface. The conditions may generally be tied to codified terms in electronic medical patient records. At step 1220, a user may rank each clinical condition. A user may enter a numerical ranking for each condition to indicate the importance of a particular condition to the desired pool. At step 1230, a user may identify each clinical condition as mandatory or optional. A designation of mandatory indicates that members of the pool must have the mandatory conditions. A designation of optional indicates that it is preferred that members of the pool have the optional conditions. At step 1240, a user may optionally assign a percentage deviation for numerical ranges. Although candidates within the numerical range are optimal, candidates within the deviation of the numerical range may be acceptable.

One or more of the steps of the methods 1100 and 1200 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of the methods 1100 and 1200 steps and/or perform the steps in a different order than the order listed. For example, some steps may not be performed in certain embodiments of the present invention. As a further example, certain steps may be performed in a different temporal order, including simultaneously, than listed above.

The system and method 1100 described above may be carried out as part of a computer-readable storage medium including a set of instructions for a computer. The set of instructions may include a first receiving routine for receiving a plurality of clinical conditions at a user interface. The set of instructions may include a second receiving routine for receiving parameters for tailoring a search of electronic medical records for the clinical conditions. The set of instructions may also include an executing routine for executing an optimization function to create a pool according to the specified conditions and parameters. The set of instructions may also include a displaying routine for displaying the pool in an order from the most optimal results to the least optimal results.

The system and method 1200 described above may be carried out as part of a computer-readable storage medium including a set of instructions for a computer. The set of instructions may include an input routine for inputting a plurality of clinical conditions at a user interface. The set of instructions may also include a ranking routine for ranking each clinical condition. The set of instructions may also include an identifying routine for identifying each clinical condition as mandatory or optional. The set of instructions may also include an assignment routine for optionally assigning a percentage deviation for numerical ranges. The set of instructions may also include a search routine for searching codified electronic medical data to create a pool of candidates according to the conditions, the rank of the conditions, the designation as mandatory, and if present, a deviation for numerical ranges. The set of instructions may also include a display routine for displaying a pool of candidates in order from the most optimal results to the least optimal results. The set of instructions may also include a selection routine for selecting a sub-set of said pool of candidates to retrieve further information for said sub-set.

Thus, in certain embodiments, local and/or centralized electronic medical record data may be used to identify participants for one or more clinical studies. In certain embodiments, a collection of codified electronic medical patient records may be searched to identify clinical study participants. A user interface allows an end-user to input a list of easily interpreted clinical conditions. The terms or conditions used may be linked or associated in a database to codified terms in the electronic medical patient records. When a search is initiated, records are screened based on the clinical condition with a greatest incidence. Once an initial pool of potential participants is identified, the clinical condition with the next largest incidence (based on a regular baseline assessment of clinical condition incidence) is used to narrow the initial pool. A narrowing screen may continue until all conditions have been met and a pool of potential study participants has been identified.

Certain embodiments consider a relative impact on total patient yield of each condition in the study protocol when applied to a collection of codified electronic medical patient records. The user interface allows the end-user to input a list of easily interpreted clinical conditions where the terms used are tied in the database to codified terms in the electronic medical patient records. When the search is concluded, the application describes each clinical condition or study parameter and its associated patient yield. The application can allow the end user to select or de-select study parameters that have a high correlation with larger total patient yield. The application also allows the end user to rank each study parameter by relative importance and then perform a refinement function where the algorithm will create the highest total patient yield for the study while helping to maximize study parameters of greatest end user importance.

In certain embodiments, a notification system acts on electronic medical record systems to alert potential investigators of relevant clinical studies, an option to 'opt-in' to the study or follow-up electronically, and may automatically re-identify patients who have previously been de-identified thru an encrypted identifier (a number assigned to each patient) and subsequently notify those patients of relevant clinical studies with similar 'opt-in' functionality as described above. This system screens databases containing highly detailed data on potential study investigators and participants and automatically notify each cohort through the electronic medical record via inbound electronic communication protocols. In doing so, this system creates great efficiency identifying potential study investigators and participants versus legacy methods due to the high specificity of the search capability that only contacts investigators and participants of study relevance and allows each to immediately 'opt-in' join the study) or request additional information through the Internet or other electronic communication network.

Thus, certain embodiments identify potential study participants in reduced time, reduced cost and/or higher quality than other methods. Certain embodiments use codified electronic medical patient records to identify potential study participants. Certain embodiments use codified electronic medical patient records to improve clinical study protocols to improve patient yield and qualities of a study participant. Certain embodiments help lower the cost and time spent recruiting investigators and participants and helps enroll participants through electronic notification via electronic medical record and associated 'opt-in' function. Further, time is not wasted on potential participants that do not truly fit the study protocol (investigator and/or patient background). Certain embodiments use codified electronic medical patient records to improve clinical study notification and recruitment to reduce time spent on inappropriate participants and allow for participants to immediately join through an electronic 'opt-in' function.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A method for searching codified electronic medical data to identify a pool of potential study candidates, said method comprising:
   receiving a plurality of conditions at a user interface;
   determining whether said condition is mandatory or optional;
   receiving a plurality of parameters for tailoring a search of said codified electronic medical data, said parameters being used to assign a weight to said optional conditions; and,
   searching said codified electronic medical data to create said pool of identifiable candidates according to whether said condition is mandatory and rank said optional weighted conditions in order from optimal to less optimal said identifiable candidates according to said optional weighted conditions.

2. The method of claim 1, further including the step of displaying said pool of candidates in order from the most optimal results to the least optimal results.

3. The method of claim 1, wherein said conditions correspond with codified terms of said codified electronic medical data.

4. The method of claim 1, wherein said parameters include ranking the conditions.

5. The method of claim 1, wherein said parameters include a designation of mandatory conditions.

6. The method of claim 1, wherein said parameters include determining a deviation for numerical ranges.

7. The method of claim 1, wherein said conditions and parameters are based on a predetermined study type.

8. The method of claim 1, wherein said parameters include determining a deviation for geographical ranges.

9. The method of claim 1, further including allowing a user to select a sub-set of said pool of candidates to retrieve contact information for said sub-set.

10. The method of claim 1, further including allowing a user to select a sub-set of said pool of candidates to retrieve electronic medical records for said sub-set.

11. A system for identifying a pool of potential study participants, said system comprising:
- a user interface for allowing input of conditions and parameters, said condition is designated mandatory or optional; said parameters being used to assign a weight to said optional conditions;
- a data storage for storing codified electronic medical data; and,
- a computer unit for executing computer software to search said codified electronic medical data according to said designated mandatory conditions and weighted optional conditions and creating a pool of identifiable candidates and ranking in order from optimal to less optimal said identifiable candidates according to said optional weighted conditions.

12. The system of claim 11, further including a display unit for displaying said pool of candidates in order from the most optimal results to the least optimal results.

13. The system of claim 11, wherein the user interface facilitates inviting one or more of the pool of potential study participants to participate in a clinical study.

14. The system of claim 11, wherein said user interface further includes an input for a predetermined study type.

15. The system of claim 14, wherein said data storage includes a database of predetermined study types.

16. The system of claim 15, wherein said each predetermined study type in said database is associated with a set of conditions and parameters.

17. A computer readable medium having a set of instructions for execution by a computer, said set of instructions comprising:
- an input routine for receiving a plurality of conditions;
- an identifying routine for identifying whether a specific condition is designated mandatory or optional;
- a selection routine for selecting a condition that is designated mandatory;
- a ranking routine for ranking said optional conditions; and
- an assignment routine for optionally assigning an acceptable percentage or absolute integer deviation for said optional condition having a numerical ranges.

18. The set of instructions of claim 17, further including a search routine for searching codified electronic medical data to create a pool of candidates according to said conditions, said rank of said conditions, said designation as mandatory, and if present, a deviation for numerical ranges.

19. The set of instruction of claim 18, further including a display routine for displaying said pool of candidates in order from the most optimal results to the least optimal results.

20. The set of instructions of claim 18, further including a selection routine for selecting a sub-set of said pool of candidates to retrieve further information for said sub-set.

* * * * *